US006703372B1

(12) United States Patent
Centellas et al.

(10) Patent No.: US 6,703,372 B1
(45) Date of Patent: Mar. 9, 2004

(54) MACROLIDES

(75) Inventors: Victor Centellas, Barcelona (ES); Rafael Garcia, Barcelona (ES); Marta Poch, Barcelona (ES); José Diago, Barcelona (ES); Johannes Ludescher, Breitenbach (AT); Immaculada Bosch, Barcelona (ES)

(73) Assignee: Biochemie S.A., Barcelona (ES)

( * ) Notice: Subject to any disclaimer, the term of this patent is extended or adjusted under 35 U.S.C. 154(b) by 32 days.

(21) Appl. No.: 10/019,500

(22) PCT Filed: Jun. 27, 2000

(86) PCT No.: PCT/EP00/05948

§ 371 (c)(1),
(2), (4) Date: Dec. 18, 2001

(87) PCT Pub. No.: WO01/00640

PCT Pub. Date: Jan. 4, 2001

(30) Foreign Application Priority Data

| Jun. 29, 1999 | (GB) | 9915216 |
| Jun. 29, 1999 | (GB) | 9915218 |
| Dec. 20, 1999 | (GB) | 9930059 |

(51) Int. Cl.$^7$ .......................... A61K 31/70; C07H 1/00; C07H 17/08
(52) U.S. Cl. .......................... 514/29; 536/7.4; 536/18.5
(58) Field of Search .................................. 536/7.4, 18.5; 514/29

(56) References Cited

U.S. PATENT DOCUMENTS 6,245,903 B1 * 6/2001 Karimian et al. ............ 536/7.4
6,268,489 B1 * 7/2001 Allen et al. ................... 536/7.4

FOREIGN PATENT DOCUMENTS

| EP | 298 650 | 1/1989 |
| EP | 827 965 (A2 A3 | 3/1998 |
| EP | 941 999 | 9/1999 |
| EP | 984 020 | 3/2000 |
| WO | WO 98/41532 | 9/1998 |
| WO | WO 00/27856 | 5/2002 |

OTHER PUBLICATIONS

Bayod–Jasanada M. et al., J. of Org. Chem., vol. 62, No. 21, pp. 7479–7481 (1997).
Wilkening, R. et al., Bioorganic & Medicinal Chemistry Letters, vol. 3, No. 6, pp. 1287–1292 (1993).

* cited by examiner

*Primary Examiner*—Elli Peselev
(74) *Attorney, Agent, or Firm*—Gabriel Lopez; Diane E. Furman

(57) ABSTRACT

Azithromycin in the form of a stable monohydrate and processes for the preparation of azithromycin in the form of an, e.g. stable, monohydrate.

11 Claims, No Drawings

MACROLIDES

The present invention relates to macrolides, e.g. azithromycin and similar compounds. Azithromycin (9-deoxo-9a-aza-9a-methyl-9a-homoerythromycin A) of formula

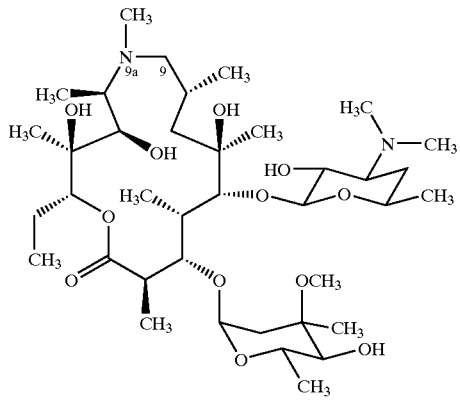

I is a well-known antibacterial agent, described e.g. in The Merck Index, 12$^{th}$ edition (1996), page 157 (946) and may e.g. be produced by Beckmann rearrangement of erythromycin A 9 oxime to give 9-deoxo-6-deoxy-6,9-epoxy-9,9a-didehydro-9a-aza-9a-homoerythromycin A of formula

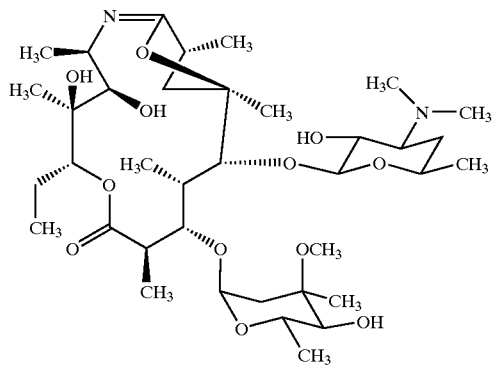

II reduction of a compound of formula II to give 9-deoxo-9a-aza-9a-homoerythromycin A of formula

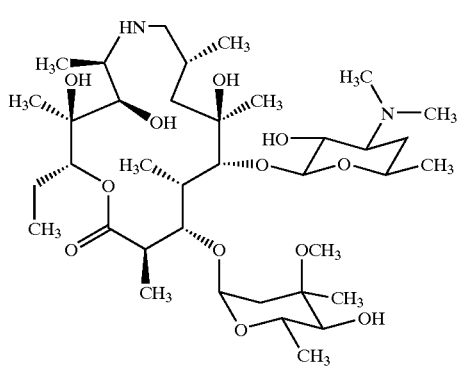

III

N-methylation of a compound of formula III to give azithromycin, e.g. of formula I.

Reduction of a compound of formula II to obtain a compound of formula III may be performed e.g. either catalytically under use of hydrogen; or, alternatively, in the presence of borohydrides, e.g. sodium borohydride, which use, however, may result in intermediate borate compounds, e.g. esters of boric acid with one or more of the hydroxy groups of a compound of formula III. The chemical nature of resulting intermediate borate compounds may be dependent on reduction conditions used and different intermediate borate compounds and mixtures thereof may be obtained. E.g. according to data (MS, $^{11}$B and $^{13}$C NMR) e.g. an intermediate borate compound of formula

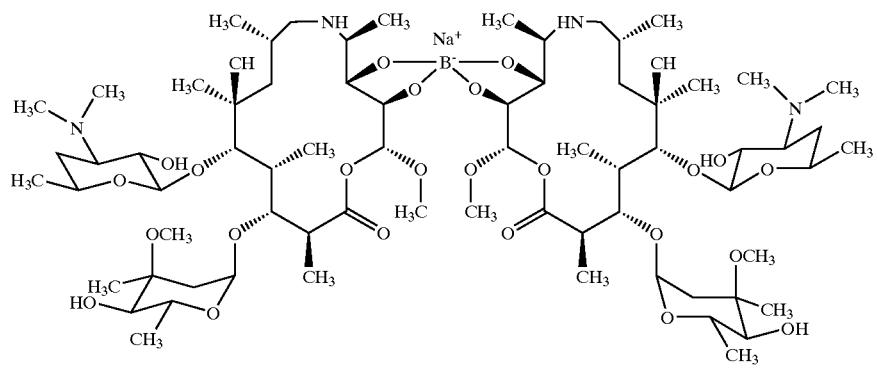

IV may be obtained. Hydrolysis of intermediate borate compounds to obtain a compound of formula III may be carried out under acidic conditions which, however, may involve degrading conditions for the macrolide structure. Isolation of the compound of formula III from a reaction mixture resulting from intermediate borate compound-hydrolysis may be performed under neutral or basic conditions and may be complicated because under neutral and basic conditions re-forming of intermediate boron compounds may occur and separation of a compound of formula III from intermediate borate compounds may e.g. afford chromatogrophy. Thus, on industrial scale, reduction of a compound of formula III is preferably carried out catalytically under use of hydrogen.

A process was now found which surprisingly facilitates the isolation of a compound of formula III in a reaction mixture resulting from intermediate borate compound-hydrolysis and which may be carried out on technical scale.

In one aspect the present invention provides a process for the production of a compound of formula III, comprising the steps
  i) treating a compound of formula II with a boronated hydride;
  ii) hydrolyzing an intermediate borate compound formed in the presence of a polyhydroxylated compound; and, if desired
  iii) isolating a compound of formula III from the reaction mixture.

In another aspect the present invention provides a process for the production of a compound of formula III, comprising the steps
  i) hydrolyzing an intermediate borate compound formed from a compound of formula II and a boronated hydride in the presence of a polyhydroxylated compound; and, if desired,
  ii) isolating a compound of formula III from the reaction mixture.

It was surprisingly found that polyhydroxylated compounds present during hydrolysis of an intermediate borate compound may result in the formation of borate ester, resulting from reaction of boric acid which is generated during hydrolysis, and hydroxy groups of a polyhydroxylated compound. Thus, re-forming of intermediate borate compounds with the macrolide, e.g. a compound of formula III, may be suppressed or avoided and isolation of a compound of formula III may be facilitated.

A process according to the present invention may be carried out as follows:

A compound of formula II which is a known compound may be treated, e.g. stirred, in a solvent, e.g. dissolved, in the presence of boronated hydride, e.g. by addition of boronated hydride to a solution of a compound of formula II (or vice versa). A solution includes a suspension wherein a compound of formula II is at least in part dissolved. A solvent includes solvent appropriate in reduction processes, preferably alcohols such as methanol, ethanol, isopropanol; and ethers, such as tetrahydrofuran; and mixtures of individual solvent, e.g. as cited above. An acid may be present, e.g. may be added to a solution of a compound of formula II, e.g. an acid which is appropriate to accelerate the reduction of imines, e.g. by formation of an iminium ion; including an organic acid, preferably formic acid or acetic acid, and an inorganic acid, preferably hydrochloric acid or sulphuric acid; and mixtures of individual acids, e.g. as cited above. E.g. an acid in aqueous solution may be added to a solution of a compound of formula II. "Boronated hydride" includes a compound containing boron and hydrogen atoms, appropriate to act as a reducing agent, such as
  boranes or diboranes, e.g. in the form of stable complexes, such as a complex with tetrahydrofuran, methyl sulfide, pyridine, morpholine, 4-methylmorpholine, 1,4-oxathiane; borane complexes with amines, e.g. including ammonia, tert-butylamine, N,N-diethylaniline, N,N-diisopropylethylamine, dimethylamine, (4-dimethylamino)-pyridine, 4-ethylmorpholine, 2,6-lutidine, triethylamine, trimethylamine; and borane complexes with phosphines e.g. with diphenylphosphine, tributylphosphine, triphenylphosphine;
  metal borohydrides, such as sodium and potassium borohydride, sodium and potassium cyanoborohydride and lithium borohydride;
  alkylborohydrides, e.g. trialkylborohydrides, e.g tri($C_{1-4}$) alkyl borohydrides, such as lithium or sodium trimethyl- and triethylborohydride;
  alkoxyborohydrides, e.g. trialkoxyborohydrides, such as tri($C_{1-4}$)alkoxyboro-hydrides, such as sodium trimethoxy-borohydride;
  acyloxyborohydrides, e.g. triacyloxyborohydrides, wherein acyl includes ($C_{2-6}$)acyl, such as sodium tri-acetoxyborohydride;
preferably sodium, potassium and lithium borohydride, sodium and lithium cyanoborohydride; and mixtures of individual boronated hydrides, e.g. as cited above; e.g. in any appropriate form, such as in solid, e.g. powder, pellet, granule form; in solution, e.g. in 2-methyoxyethylether, triethylene glycol dimethyl ether, aqueous solution, e.g. sodium hydroxide solution; e.g. fixed onto a carrier, such as alumina.

An intermediate borate compound, e.g. a borate ester, e.g. such as described above, e.g. of formula IV, may be formed in the reaction mixture and may be isolated, e.g. as conventional, e.g. by evaporating the solvent (system); or e.g. by hydrolyzing an excess of boronated hydride in the reaction mixture, e.g. by treating the reaction mixture with aqueous, e.g. inorganic, acid, adjusting the pH of the mixture obtained to a basic pH, and isolating an intermediate borate compound which may precipitate, e.g. by filtration; or extracting an intermediate borate compound into a solvent which is able to form a two-phase system with water and which is able to dissolve an intermediate borate compound in a two-phase system with water; such as a halogenated hydrocarbon, e.g. methylene chloride; and, if desired evaporating off the solvent.

The amount of a boronated hydrate in respect with a compound of formula II is not critical. An appropriate amount may be easily determined by pre-testing.

An, e.g. isolated, intermediate borate compound obtained may be hydrolized, e.g. in a solvent, e.g. in solution, such as an aqueous solution, e.g. water or an organic solvent which is inert under the reaction conditions and which contains water, e.g. in the presence of an acid, e.g. an inorganic acid, such as hydrochloric acid, sulphuric acid and in the presence of a polyhydroxylated compound, e.g. by addition of a polyhydroxylated compound to a solution (including a suspension) of an intermediate borate compound. An intermediate borate compound obtained in a solution of a solvent which forms a two-phase system with water may e.g. be extracted into an acidic aqueous solvent and a polyhydroxylated compound may be added to the acidic mixture obtained.

A polyhydroxylated compound includes an organic compound having two or more hyroxyl groups, e.g.
  linear polyalcohols, such as ethyleneglycol, propyleneglycol, glycerol, 1,2-hexanediol, 1,6-hexanediol, 2,5-hexanediol, 1,2,3-hexanetriol, 1,2,6-hexanetriol or pentaerythritol; linear polyalcohols, e.g. as cited above, having beside at least two hydroxyl groups further functional groups, e.g. amine group(s), such as diethanolamine or triethanolamine;

cyclic polyalcohols; e.g. exo-cyclic polyalcohols such as exo-2,3-norbornanediol;

sugar-type polyalcohols, e.g. monosaccarides, such as glyceralhehyde, erythrose, erythrulose, arabinose, lyxose, ribose, ribulose, xylose, xylulose. allose, altrose, fructose, galactose, glucose, mannose, sorbose, tagatose and tallose, e.g. in any of its isomeric forms (D-form, L-form or DL form);

sugar-type polyalcohols obtainable by reduction of corresponding sugars, such as erythrol, threitol, arabitol, xylitol, adonitol, sorbitol, dulcitol, manitol;

sugar-type polyalcohols having beside at least two hydroxy groups further functional groups, e.g. amines such as glucamine or N-methylglucamine;

a resin, e.g. an ion exchange resin, containing hydroxy groups, e.g. Amberlite IRA-743 resin, e.g. as offered in the Catalogue Handbook of Fine Chemicals (1996–1997), in any appropriate form, e.g. in solid form, in solution, fixed onto a carrier.

The amount of a polyhydroxy compound to respond with an intermediate borate compound is not critical. An appropriate amount may be easily determined by pre-testing.

A compound of formula III may be obtained and may be isolated from the reaction mixture, e.g. as conventional, e.g. by filtration; or e.g. may be extracted into a solvent which is able to form a two-phase system with water and which is able to dissolve a compound of formula III in a two-phase system with water; e.g. a two-phase system may be obtained, the phases may be separated and the solvent of the organic phase may be removed, e.g. by evaporation, e.g. to dryness; or a solution of a compound of formula III may be used as such, e.g. without further isolation or purification, in a methylation reaction, e.g. to obtain azithromycin.

In a further aspect the present invention provides a process for the production of azithromycin, e.g. of formula I, e.g. in the form of a solvate, comprising i) treating a compound of formula II with a boronated hydride, ii) hydrolyzing an intermediate borate compound formed in the presence of a polyhydroxylated compound to obtain a compound of formula III, and iii) methylating a compound of formula III obtained in step ii) at the amine group in position 9a of the erythromycin ring structure; and, if desired, iv) isolating azithromycin; e.g. in the form of a solvate, e.g. in the form of a hydrate, such as a dihydrate or a monohydrate.

In another aspect the present invention provides a process for the production of azithromycin, e.g. of formula I, e.g. in the form of a solvate, comprising the steps i) hydrolyzing an intermediate borate compound formed from a compound of formula II and a boronated hydride in the presence of a polyhydroxylated compound;

ii) methylating a compound of formula III obtained in step ii)at the amine group in position 9a of the erythromycin ring structure; and iii) isolating azithromycin; e.g. in the form of a solvate, e.g. in the form of a hydrate, such as a dihydrate or a monohydrate.

In a further aspect the present invention provides the use of a compound of formula III obtained by hydrolyzing an intermediate borate compound formed from a compound of formula II and a boronated hydride, in the presence of a polyhydroxylated compound in the production of azithromycin, e.g. in the form of a solvate, e.g. in the form of a hydrate, such as a dihydrate or a monohydrate.

Methylation of a compound of formula III at the amine group in position 9a of the erythromycin ring structure may be carried out as appropriate, e.g. according to a method as conventional, e.g. treating a solution of a compound of formula III in a solvent, e.g. ethyl acetate, with formic acid and aqueous formaldehyde and isolating azithromycin obtained.

Processes according to the present invention are useful in the production of azithromycin. Advantages includes e.g. high yields in the production of desired compounds, e.g. of formula III and of azithromycin; a compound of formula III may be obtained in pure form and may be used without further purification or even without isolation in a subsequent reaction, e.g. in a methylation step; the processes may be used on industrial scale.

Azithromycin, e.g obtainable according to a process of the present invention, may be in the form of a solvate, e.g. in the form of a hydrate, such as a monohydrate or e.g. in the form of a dihydrate. It is known that azithromycin in the form of a monohydrate is unstable, e.g. the crystall structure of azithromycin in the form of a monohydrate may break down under normal air humidity conditions within some hours. Thus, azithromycin in the form of a monohydrate which may be obtained according to a conventional method, e.g. by precipitation with water from ethanolic solution, is described to be not easy to handle. This might be one reason why azithromycin currently on the market is in the form of a dihydrate which is known to be stable under normal air humidity conditions, e.g. the crystall structure of azithromycin in the form of a dihydrate is known not to break down within some hours under normal air humidity conditions.

Azithromycin in the form of a monohydrate produced according to known methods, e.g. precipitation with water from an ethanolic solution, may beside its unstability contain a high content of residual solvents, e.g 1.0% and more and may be inappropriate for use as a pharmaceutical.

It was now surprisingly found that azithromycin, e.g. of formula I, may be obtained in the form of an, e.g. crystalline, monohydrate which is stable and which may be easy to handle. "Stable monohydrate" as used herein includes a compound of formula I in the form of a monohydrate which is crystalline and which maintains its crystalline structure for at least 24 hours, e.g. for several weeks, under normal, e.g. normal air humidity, conditions. The crystalline structure of azithromycin in the form of a monohydrate may be determined by its (known) X-ray powder diffraction pattern.

In another aspect the present invention provides azithromycin, e.g. of formula I, in the form of a stable, e.g. crystalline, monohydrate.

It was also found that azithromycin in the form of a stable monohydrate according to the present invention may contain water from, e.g. about, 1.5%, e.g. and more, such as 2.0%; up to 5.5% and more; e.g. 6.0% w/w, e.g. 2.0% to 6.0% w/w; such as 1.5% to 5.5% w/w without changing its crystalline structure and without taking up remarkably further water. A water content of 2.0% to 6.0% w/w includes the water necessary for azithromycin monohydrate formation.

In another aspect the present invention provides a composition comprising, e.g. consisting essentially of; azithromycin, e.g. of formula I, in the form of a stable monohydrate, e.g. crystalline; e.g. showing an X-ray powder diffraction pattern corresponding to azithromycin in the form of a monohydrate, e.g. even after 24 hours under normal air humidity conditions; and 2.0% to 6.0% w/w of water.

It was also found that azithromycin in the form of a stable, e.g. crystalline, monohydrate may be produced by removing organic solvent from a solution of azithromycin in organic solvent; e.g. whereas azithromycin produced according to prior art, e.g. by precipitation with water from ethanolic solution may result in azithromycin in the form of an unstable monohydrate.

In another aspect the present invention provides a process for the production of azithromycin in the form of a stable monohydrate, e.g. crystalline, comprising removing organic solvent from a solution of azithromycin in organic solvent.

A process according to the present invention may be carried out as follows:

Azithromycin in any form, e.g. in free base form; and in the form of a salt, e.g. in the form of a hydrochloride, e.g. a dihydrochloride, acetate; and/or in the form of a solvate, e.g. in the form of an (unstable) monohydrate or in the form of a dihydrate; and in non-solvate form, e.g. anhydrous form, may be used as a starting material and may be dissolved, e.g. suspended, in organic solvent. A solution of azithromycin in organic solvent may be obtained. A "solution" includes a suspension, in which at least a part of azithromycin is dissolved. Organic solvent includes solvent which is appropriate to dissolve azithromycin, preferably water-miscible organic solvent. Water-miscible organic solvent includes organic solvent which may form a one-phase system with water, preferably water-miscible ketones such as acetone; lower alcohols, e.g. ($C_{1-4}$)alcohols, such as methanol, ethanol, isopropanol; lower alkyl acetates, such as methyl acetate, ethyl acetate; and acetic acid and formic acid amides, such as dimethyl acetamide, N,N-diemthylformamide; or a mixture of individual organic solvents, e.g. as listed above. Water may be present in organic solvent. An appropriate temperature for the production of a solution of azithromycin in organic solvent includes a temperature at which azithromycin is not degraded, including, e.g. a temperature range of –20° C. to 70° C., such as 0° C. to 50° C. If as a starting material azithromycin is used in the form of a salt, a base may be used to provide azithromycin in solution in the form of a free base, e.g. to obtain an appropriate pH of a solution of azithromycin, e.g. an pH where azithromycin is in the form of a free base, e.g. by addition of a base to a mixture of azithromycin in in the form of a salt with organic solvent, e.g. according to a method as conventional. The concentration of a solution of azithromycin in organic solvent is not critical; preferably a saturated or almost saturated solution may be used. An amount of water which is necessary for the formation of azithromycin in the form of a monohydrate may be present in the organic solvent. If a solution of azithromycin in organic solvent contains less water than necessary for azithromycin monohydrate formation, water may be added, e.g. sufficient water to form azithromycin monohydrate. If a solution of azithromycin in organic solvent contains more water, e.g. an excess of water, than necessary for azithromycin monohydrate formation, excess of water may be removed, if desired, but not necessarily. Appropriate methods for removal of excess of water includes methods as conventional, e.g. removing, e.g. distilling off, organic solvent, e.g. preferably lower alcohols, lower alkyl acetates or acetic and formic acid amides, together with water from a solution of azithromycin in organic solvent; or addition of a drying agent, e.g. such as conventional in organic chemistry, e.g. sodium sulphate, prior to organic solvent removal of a solution of azithromycin in organic solvent, preferably in lower ketones. Organic solvent from a solution of azithromycin in organic solvent may be removed, e.g. partially or (almost) completely, e.g. by a method as conventional, e.g. by distillation, such as evaporation.

Alternatively, azithromycin in the form of a monohydrate having a water content which is at least in the range of azithromycin in the form of a monohydrate, or higher, e.g. unstable azithromycin in the form of a monohydrate, or azithromycin in the form of a dihydrate may be warmed up to an appropriate temperature, e.g. as described above, in organic solvent, e.g. in lower alcohols, to form a solution of azithromycin in alcohol; and the solution may be cooled to obtain azithromycin, e.g. crystalline, in the form of a stable monohydrate. In order to increase yields alcohol may be removed from a correspondingly obtained crystal suspension of azithromycin in the form of a stable monohydrate in alcohol.

Azithromycin in the form of a stable monohydrate may precipitate, e.g. in crystalline form and may be isolated, e.g. as conventional, e.g. by filtration or centrifugation. An anti-solvent with the exception of water, e.g. an organic solvent which decreases the solubility of azithromycin in organic solvent solution, may be added to a residue obtained by organic solvent removal in order to increase yields.

In another aspect the present invention provides a process for the production of azithromycin in the form of a stable monohydrate comprising dissolving azithromycin in an alcohol, and crystallizing azithromycin in the form of a stable monohydrate from the alcoholic solution.

In another aspect the present invention provides a process for the production of azithromycin in the form of a stable monohydrate comprising dissolving azithromycin in the form of a dihydrate in organic solvent, e.g. ethanol, isopropanol, methyl acetate; e.g. or a or a mixture of individual solvents listed, distilling off water-miscible organic solvent and, if desired, e.g. and if present, excess of water; and isolating azithromycin in the form of a stable monohydrate.

In another aspect the present invention provides a process for the production of azithromycin in the form of a stable monohydrate comprising dissolving azithromycin in the form of a dihydrate in organic solvent, e.g. acetone, e.g., if desired drying the solution obtained, e.g. by addition of a drying agent; distilling off water-miscible organic solvent and isolating azithromycin in the form of a stable monohydrate.

In a further aspect, the present invention provides a composition containing, e.g. consisting essentially of; azithromycin in the form of a monohydrate, e.g. solid, e.g. crystalline, e.g. stable; and methyl acetate, acetone or isopropanol.

It was also surprisingly found that azithromycin, e.g. of formula I, may be obtained in the form of an, e.g. crystalline, monohydrate, e.g. which is stable, and which may be easy to handle; and which may have a low content of (residual) organic solvent, e.g. a content of organic solvent, e.g. including organic solvent whith low toxic potential (e.g. Class 3 solvents); of 0.5% w/w and lower; e.g. amounts which are on the lower end of analytical detectability, such as 0.001%, e.g. 0.002%, e.g. 0.003%, e.g. 0.1% to 0.5%; e.g. and less; e.g. fulfilling European Pharmacopoeia specifications. E.g azithromycin in the form of a monohydrate, e.g. stable, e.g. crystalline, having a low organic solvent content in an amount of the lower end of analytical detectability up to 0.5%; e.g. and even lower; may be e.g. obtained as described above, or, e.g. more specifically, as follows:

Azithromycin in any form, e.g. in a form as described above as a starting material for the production of azithromycin in the form of a stable monohydrate, may be used as a starting material. A solution of azithromycin in the form of a salt in a solvent may be produced, e.g. either by dissolving azithromycin in form of a salt in a solvent; or by conversion of azithromycin in free form in a solvent into the form of a salt of azithromycin; e.g. by addition of an acid to azithromycin in solvent. A "solvent" includes a suspension, in which at least a part of azithromycin in the form of a salt is dissolved. Appropriate acids includes, e.g. an organic acid, for example formic acid or acetic acid, and an inorganic acid, for example hydrochloric, hydrobromic, nitric or sulphuric acid, preferably hydrochloric acid or sulphuric acid. Solvent includes solvent which is appropriate to dissolve azithromycin in the form of a salt, e.g. including aqueous solvent. Aqueous solvent includes water or a mixture of water with organic solvent, e.g. one or more organic solvents, for example water miscible and water immiscible organic solvent, such as alcohols, e.g. methanol, ethanol, isopropanol; ketones such as acetone, methyl isobutyl ketone; alkyl esters such as alkyl esters, e.g. ($C_{1-4}$)alkyl; of formic or acetic acid, e.g. methyl acetate, ethyl acetate, isopropyl acetate, butyl acetate; aromatic hydrocarbons such as toluene, xylenes; ethers, such as tetrahydrofuran, methyl t-butyl ether; chlorinated hydrocarbons such as methylene chloride; and amides such as monoalkyl and dialkyl amides, e.g. N-methyl formamide, N,N-dimethylacetamide, N,N-dimethylformamide; preferably water or a mixture of water with one or more alcohols, ketones, alkyl acetates; e.g. water, or aqueous solvent, such as water or water containing 0.5% to 2% v/v; such as 1% to 15% v/v of organic solvent.

Appropriate reaction conditions for the production of a solution of azithromycin in the form of a salt according to the present invention include, e.g.

(i) A temperature at which azithromycin is not degraded, including, e.g. a temperature range of −20° C. to 90° C., such as 0° C. to 70° C.;

(ii) An appropriate pressure, e.g. atmospheric pressure, and a pressure which is above or below atmospheric pressure;

(iii) Appropriate dilution, e.g. a dilution range of 1 g to 500 g of azithromycin in the form used as a starting material, per liter of solvent.

A resulting solution of azithromycin in the form of a salt in a solvent may be purified as appropriate, e.g. by filtration, charcoal treatment; in order to remove impurities. The pH of an, e.g. purified, solution of azithromycin in the form of a salt may be adjusted to an pH where azithromycin is present in free form, including e.g. a pH of, e.g. ca., 8.0 to 13.0, such as 9.0 to 12.0, e.g. 10.0 to 11.0; e.g. by addition of a base to a solution of azithromycin in the form of a salt in a solvent. A "solution" of azithromycin in free form includes a suspension, in which at least a part of azithromycin in free form is dissolved. Appropriate bases include bases which are suitable for pH adjustment, e.g. an inorganic base, such as ammonia or an alkali-, e.g. sodium, potassium; earth alkali-, e.g. calcium, magnesium; and ammonium-; -hydroxide, -carbonate, -hydrogencarbonate; and an organic base, such as an amine, e.g. an alkyl amin, or a mixture of individual bases, e.g. as described above. A base may be preferably a hydroxide, e.g. sodium or ammonia; preferably in aqueous solution.

Azithromycin in free form and in the form of an e.g. stable; monohydrate, e.g. crystalline; may precipitate from the solution and may be isolated, e.g. according to a method as conventional, e.g. by centrifugation or filtration, and may be dried, for example at appropriate temperatures, e.g. including a range of, e.g. ca., 30° C. to 80° C. Azithromycin, e.g. crystalline, in the form of an, e.g. stable; monohydrate may be obtained; e.g. a composition of azithromycin in the form of an, e.g. stable, monohydrate and less than 0.5% w/w of organic solvent; e.g. a composition comprising, e.g. consisting essentially of; azithromycin in the form of a stable monohydrate and more than 0% to 0.5% w/w of organic solvent; e.g. analytically detectable amounts of organic solvent up to 0.5% w/w; e.g. and containing 2.0% to 6.0% w/w of water.

In another aspect the present invention provides a process for the production of azithromycin in the form of an, e.g. stable, monohydrate, e.g. crystalline, comprising the steps of i) adjusting the pH of a solution of azithromycin in the form of a salt, and ii) isolating azithromycin of formula I in the form of an, e.g. stable, monohydrate, characterised in that the solution of azithromycin in step i) is an aqueous solution wherein the solvent is selected from water or a mixture of water and organic solvent.

In another aspect the present invention provides a composition comprising, e.g. consisting essentially of; azithromycin, e.g. of formula I, in the form of an, e.g. crystalline, monohydrate, e.g. stable; and organic solvent in an amount of 0.5% w/w and lower; e.g. and an amount which is higher than 0% w/w; e.g. an analytically detectable amount up to 0.5% w/w; e.g. an amount which fulfils European Pharmacopoeia specifications.

When solely water is used as a solvent according to the present invention, azithromycin in the form of an, e.g. stable, monohydrate, e.g. crystalline, may be obtained, substantially free of organic solvent.

In another aspect the present invention provides azithromycin in the form of a monohydrate, substantially free of organic solvent.

Azithromycin in the form of a stable monohydrate according to the present invention; e.g. and a composition of azithromycin in the form of a monohydrate, e.g. stable, and an analytically detectable amount up to 0.5% w/w of organic solvent; and azithromycin in the form of an, e.g. stable, monohydrate substantially free of organic solvent; is useful in the production of a pharmaceutical composition containing azithromycin as an active ingredient.

In another aspect the present invention provides a pharmaceutical composition, comprising, e.g. essentially consisting of, azithromycin in the form of a stable monohydrate; or a composition of azithromycin in the form of a monohydrate, e.g. stable, and an analytically detectable amount up to 0.5% w/w/ of organic solvent; or azithromycin in the form of an, e.g. stable, monohydrate substantially free of organic solvent;

in association with at least one pharmaceutical carrier or diluent.

A pharmaceutical composition comprising, e.g. essentially consisting of, azithromycin in the form of a stable monohydrate as an active ingredient; or a composition of azithromycin in the form of a monohydrate, e.g. stable, and an analytically detectable amount up to 0.5% w/w of organic solvent; or azithromycin in the form of an, e.g. stable, monohydrate substantially free of organic solvent;

according to the present invention may contain the same concentrations of azithromycin and may be used for the same indications in the same dosage ranges as a known pharmaceutical composition containing azithromycin in the form of a dihydrate as an active ingredient, e.g. as is currently on the market.

The following examples illustrate the present invention. All temperatures are given in degree Celsius and are uncorrected.

The X-ray powder diffraction pattern and the IR spectrum of azithromycin in the form of a monohydrate obtained according to the following examples corresponding to that of known (unstable) azithromycin in the form of a monohydrate.

Azithromycin in the form of a monohydrate obtained according to the following examples maintains its crystallinity and its X-ray powder diffraction pattern when kept for several weeks under normal air humidity conditions.

Water content (% w/w) is determined by the K. Fischer method and includes the water necessary for azithromycin monohydrate formation where indicated.

Residual solvent (% w/w) is determined by GC, headspace method.

EXAMPLE 1

To a solution of 35.62 g of a compound of formula II (assay 92.8%) in 180 ml of methanol, cooled to −10/−15°, 14.25 g of sodium borohydride are added during ca. 2 hours. The reaction mixture obtained is kept at −10/−15° for ca. further 2 hours, heated to 55°, cooled to 20° and the solvent is evaporated off. The residue obtained (108.9 g) is dissolved in a mixture of methylene chloride and water and is stirred at room temperature for ca. 30 minutes. A two-phase system is formed. The organic phase is separated off and the aqueous phase is extracted with methylene chloride. The organic phase is dried over sodium sulphate and the solvent is evaporated off.

31.15 g of a residue are obtained. The residue obtained is an intermediate borate compound and believed to be a compound of formula IV, e.g. confirmed by the following data:

Elemental analysis: Theory: B: 0.7%; Na: 1.0%. Found: B: 0.6%; Na: 1.1% MS-FAB (−): 1476 ($M^+$−$Na^+$+$H^+$). An $^{11}$B-NMR spectrum shows a ppm signal in the expected range of a tetracoordinated boron bond to four oxygen atoms..

EXAMPLE 2

1.98 g of an intermediate borate compound obtained according to example 1 are suspended in 34 ml of water. 20% sulphuric acid is added to the suspension obtained and a pH of 2.8.is adjusted. 22 g of an ion resin containing hydroxy groups (Amberlite IRA-743) are added to the mixture obtained and the mixture obtained is stirred for ca. 30 minutes, the resin is filtrated off and washed with water. The pH of the filtrate obtained is adjusted to a basic pH with 20% sodium hydroxide. The mixture obtained is extracted with ethyl acetate, the organic phase is dried and evaporated off.

Yield: 1.22 g of a compound of formula III in pure form.

EXAMPLE 3

Is carried out according to the method as described in example 2 but using 1.82 g of N-methyl-D-glucamine instead of 10.22 g of Amberlite IRA-743 resin.

Yield: 1.33 g of a compound of formula III.

EXAMPLE 4

Is carried out according to the method as described in example 2 but using 10.02 g of an intermediate borate compound obtained according to example 1 instead of 1.98 g, 170 ml of water instead of 34 ml and 8.60 g of sorbitol instead of 10.22 g of Amberlite IRA-743 resin.

Yield: 8.50 g of a compound of formula III.

EXAMPLE 5

6.48 g of a compound of formula III obtained according to example 4 are dissolved in 58 ml of ethyl acetate and 0.6 ml of formic acid and 1.30 ml of 37% aqueous formaldehyde are added to the solution obtained. The mixture obtained is refluxed for ca. 2 hours. HPLC analysis shows the formation of azithromycin.

Yield: 77%.of theory.

EXAMPLE 6

70.0 g of azithromycin dihydrate are dissolved in 280 ml of methyl acetate at 25°. The resulting solution is heated to 55–60° and 225 ml of methyl acetate are distilled off. the distillation residue is cooled to 20°. Azithromycin in the form of a monohydrate crystallizes, is filtrated off and dried.

Yield: 47.5 g. Water content: 2.5%

EXAMPLE 7

15.0 g of azithromycin dihydrate are dissolved in 75 ml of acetone, anhydrous sodium sulphate is added, the mixture obtained is stirred for ca. 10 minutes and the solid is filtrated off and washed with 15 ml of acetone. From the solution obtained 57 ml of acetone are distilled off and the resulting suspension is cooled to room temperature. Azithromycin in the form of a monohydrate crystallizes, is filtrated off and dried.

Yield: 7.3 g. Water content: 2.6%

EXAMPLE 8

10.0 g of azithromycin dihydrate are suspended in 10 ml of absolute ethanol and the mixture is heated. A clear solution is obtained, which is cooled slowly to room temperature and stirred at ca. 25° for ca. one hour. Azithromycin in the form of a monohydrate crystallizes. Ethanol is evaporated off and azithromycin in the form of a monohydrate is filtrated off and dried.

Yield: 5.26 g. Water content: 1.9%

EXAMPLE 9

Example 8 is repeated but using 10 ml of isopropanol instead of 10 ml of absolute ethanol. Crystalline azithromycin in the form of a monohydrate is obtained.

Yield: 6.0 g, Water content: 2.5%.

EXAMPLE 10

20 g of azithromycin in the form of a dihydrate, suspended in 40 ml of water are treated with 2N HCl. A solution is obtained, is filtered and the filtrate is added dropwise to 80 ml of water keeping the pH between 10 and 11 by addition of 0.5 N sodium hydroxide at a temperature of ca. 55°. The suspension obtained is cooled to room temperature and stirred for ca. 30 minutes. A solid precipitate obtained is filtrated off, washed with water and dried. 18.2 g of azithromycin in the form of a monohydrate are obtained. Water content: 3.7%. Residual solvent: acetone 0.01%.

Azithromycin assay on anhydrous basis (HPLC): 98.6%.

EXAMPLE 11

Example 10 is repeated, but using a mixture of 80 ml of water and 4 ml of ethanol instead of 80 ml of water in the precipitation step; 19.5 g of azithromycin in the form of a monohydrate are obtained. Water content: 2.9%.

Residual solvents: acetone 0.003%, ethanol 0.002%.

What is claimed is:

1. A process for the production of a compound of formula III

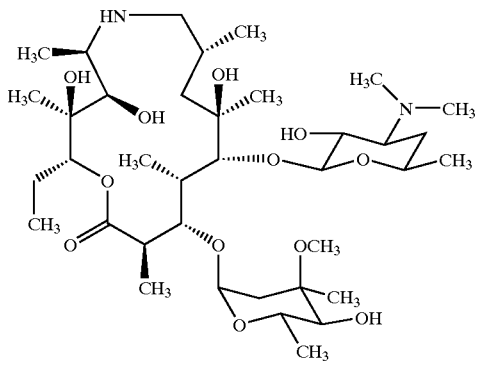

comprising the steps
  i) treating a compound of formula II

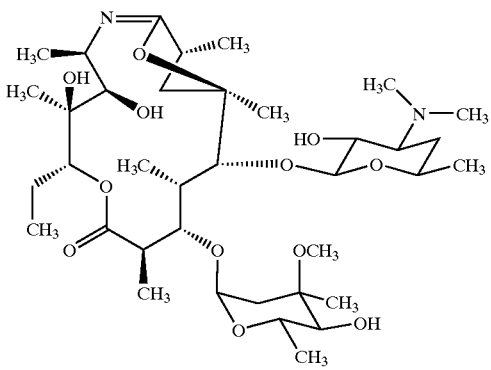

with a boronated hydride;
  ii) hydrolyzing an intermediate borate compound formed in the presence of a polyhydroxylated compound; and, if desired,
  iii) isolating a compound of formula III from the reaction mixture.

2. A process for the production of azithromycin, comprising
  i) treating a compound of formula II as defined in claim 1, with a boronated hydride,
  ii) hydrolyzing an intermediate borate compound formed in the presence of a polyhydroxylated compound to obtain a compound of formula III as defined in claim 1,
  iii) methylating a compound of formula III obtained in step ii) at the amine group in position 9a of the erythromycin ring structure; and, if desired,
  iv) isolating azithromycin.

3. A process of claim 2 wherein the azithromycin is in the form of a solvate.

4. A process for the production of azithromycin comprising the steps
  i) hydrolyzing an intermediate borate compound formed from a compound of formula II, as defined in claim 1, and a boronated hydride in the presence of a polyhydroxylated compound;
  ii) methylating a compound of formula III, as defined in claim 1, at the amine group in position 9a of the erythromycin ring structure; and
  iii) isolating azithromycin.

5. A process of claim 4, wherein the azithromycin is isolated in the form of a solvate.

6. A process for the production of azithromycin in the form of a monohydrate comprising the steps of
  i) adjusting the pH of a solution of azithromycin in the form of a salt, wherein the solvent is only water; and
  ii) isolating azithromycin in the form of a monohydrate.

7. A process of claim 6, wherein the pH in step i) is adjusted to 8.0–13.0.

8. A process of claim 6, wherein the pH in step i) is adjusted to 10.0–11.0.

9. Azithromycin obtained by the process of claim 6 having an analytically detectable amount up to 0.5% w/w of organic solvent.

10. Azithromycin in the form of a monohydrate having an analytically detectable amount up to 0.5% w/w of organic solvent.

11. A pharmaceutical composition comprising
  monohydrate;
  a composition of azithromycin in the form of a monohydrate and an analytically detectable amount up to 0.5% w/w of organic solvent;
  in association with at least one pharmaceutical carrier or diluent.

* * * * *